United States Patent
Schulze et al.

(10) Patent No.: US 11,599,372 B2
(45) Date of Patent: *Mar. 7, 2023

(54) CONTROLLING PERMISSIONS FOR ACCESS TO USER INTERFACE FEATURES

(71) Applicant: LIFETRACK MEDICAL SYSTEMS PRIVATE LTD., Singapore (SG)

(72) Inventors: Eric Schulze, Taguig (PH); Brendan Philip Rees, Quezon (SG)

(73) Assignee: Lifetrack Medical Systems Private Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/705,053

(22) Filed: Mar. 25, 2022

(65) Prior Publication Data

US 2022/0350623 A1    Nov. 3, 2022

Related U.S. Application Data

(60) Continuation of application No. 16/835,589, filed on Mar. 31, 2020, now Pat. No. 11,334,373, which is a
(Continued)

(51) Int. Cl.
*G06F 3/0482* (2013.01)
*G06F 9/451* (2018.01)
(Continued)

(52) U.S. Cl.
CPC ............ *G06F 9/451* (2018.02); *G06F 3/0482* (2013.01); *G06F 40/177* (2020.01); *G06F 40/197* (2020.01); *G16H 15/00* (2018.01)

(58) Field of Classification Search
None
See application file for complete search history.

(56) References Cited

U.S. PATENT DOCUMENTS 6,460,141 B1    10/2002    Olden
9,276,958 B2    3/2016    Hagiwara et al.
(Continued)

FOREIGN PATENT DOCUMENTS

| CN | 104091130 | 10/2014 |
| WO | WO 2015/095597 | 6/2015 |
| WO | WO 2018/011717 | 1/2018 |

OTHER PUBLICATIONS

Australian Examination Report for AU Application No. 2018359869, dated Oct. 2, 2020, 5 pages.
(Continued)

*Primary Examiner* — Rinna Yi
(74) *Attorney, Agent, or Firm* — Fish & Richardson P.C.

(57) ABSTRACT

Among other things, instances of at least one type of page of a user interface are presented to at least a first user and a second user. Each instance includes a current scope of user interface elements. All of the instances have current scopes that are the same as or subsets of a prototype scope of user interface elements for that type of page. A permitted scope of user interface elements are available to each corresponding user. The permitted scope of the second user is the same as or a subset of the permitted scope of the first user. Selections of user interface elements to be included in an updated scope are received from the first user. The selections include only user interface elements that belong to both the prototype scope for that type of page and the permitted scope of the first user.

18 Claims, 4 Drawing Sheets

Figure 1:
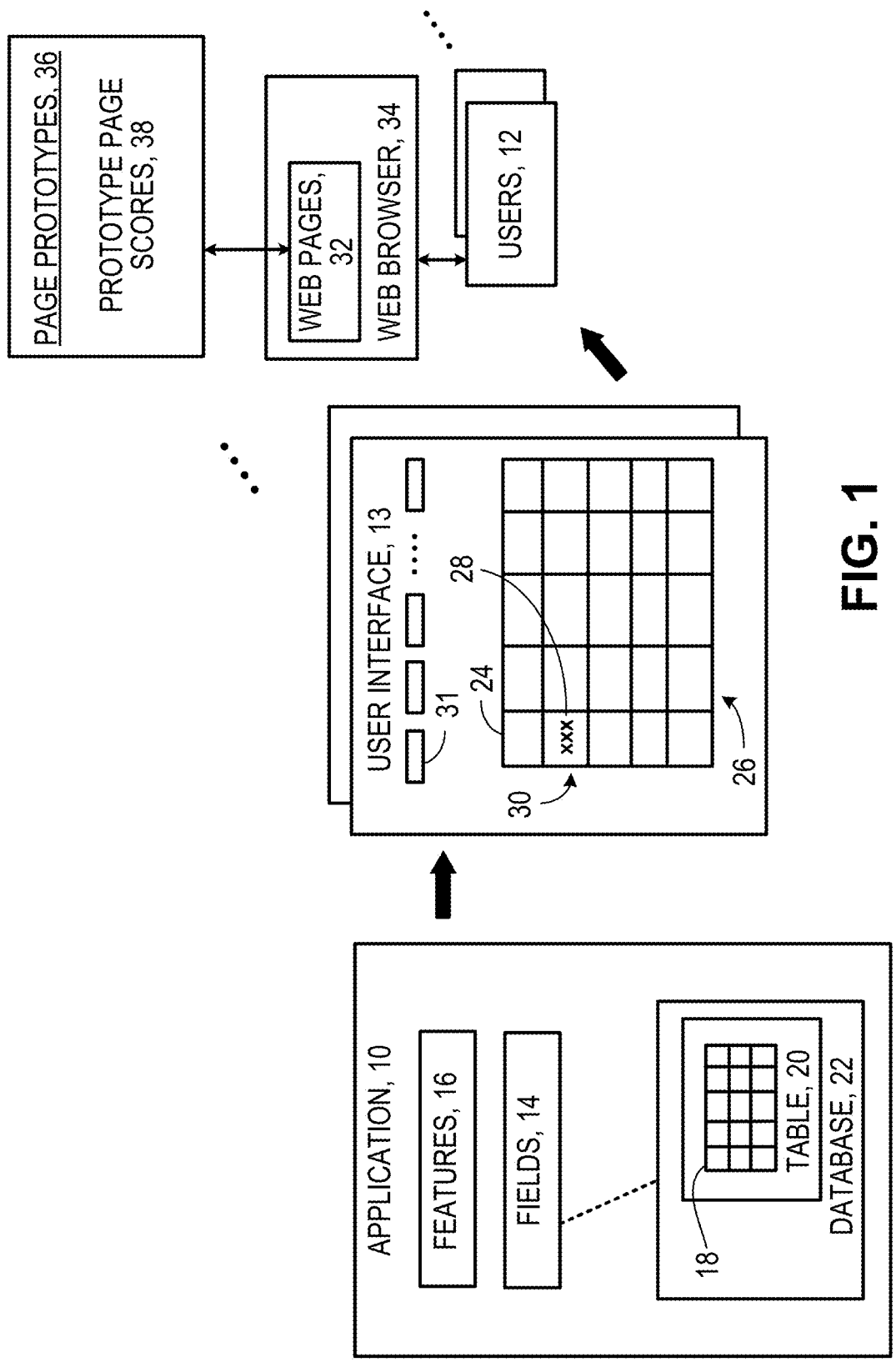

Related U.S. Application Data division of application No. 15/804,131, filed on Nov. 6, 2017, now Pat. No. 10,642,451.

(51) Int. Cl.
*G16H 15/00* (2018.01)
*G06F 40/177* (2020.01)
*G06F 40/197* (2020.01)

(56) References Cited

U.S. PATENT DOCUMENTS

| | | |
|---|---|---|
| 9,705,931 B1 | 7/2017 | Schulze et al. |
| 10,339,286 B2 | 7/2019 | Schulze et al. |
| 10,642,451 B2 | 5/2020 | Schulze et al. |
| 10,650,127 B2 | 5/2020 | Schulze et al. |
| 11,334,373 B2 | 5/2022 | Schulze et al. |
| 2002/0157023 A1 | 10/2002 | Callahan et al. |
| 2005/0075544 A1 | 4/2005 | Shapiro |
| 2008/0046442 A1 | 2/2008 | Grason |
| 2009/0300544 A1 | 12/2009 | Psenka |
| 2010/0070897 A1 | 3/2010 | Aymeloglu |
| 2011/0213634 A1 | 9/2011 | Karakey |
| 2011/0277017 A1 | 11/2011 | Ivanov et al. |
| 2012/0290920 A1 | 11/2012 | Crossley |
| 2014/0215604 A1 | 7/2014 | Giblin |
| 2015/0320365 A1 | 11/2015 | Schulze et al. |
| 2015/0324075 A1 | 11/2015 | Schulze et al. |
| 2016/0124581 A1 | 5/2016 | Schulze et al. |
| 2016/0328577 A1 | 11/2016 | Howley |
| 2018/0018448 A1 | 1/2018 | Schulze et al. |
| 2019/0138161 A1 | 5/2019 | Schulze et al. |
| 2019/0311091 A1 | 10/2019 | Schulze et al. |
| 2020/0272285 A1 | 8/2020 | Schulze et al. |
| 2020/0293637 A1 | 9/2020 | Schulze et al. |

OTHER PUBLICATIONS

Australian Examination Report for Australian Application No. 2017296139, dated Sep. 10, 2019, 7 pages.
Dolgobrod, Maxim, "Developing a user interface for a cross-platform web application", Helsinki Metropolia University of Applied Sciences, Master's Thesis, Information Technology, May 30, 2013 (99 pages).
IN Examination Report in IN Appln. No. 201947003415, dated Aug. 14, 2020, 6 pages.
International Preliminary Report on Patentability for International Application No. PCT/US2018/059392, dated May 12, 2020, 14 pages.
International Search Report and Written Opinion from PCT application PCT/US2018/059392, dated Jan. 29, 2019, 15 pages.
Samarati et al., "Access control: Policies, Models, and Mechanisms," Foundations of Security Analysis and Design: Tutorial Lectures, Sep. 2000, 2171:137-196.
Sandhu et al., "Access control: principle and practice," IEEE Communications Magazine, Sep. 1994, 32(9):40-48.
USPTO Transaction History for U.S. Appl. No. 15/209,486, filed Jul. 13, 2016, 140 pages.
USPTO Transaction History for U.S. Appl. No. 15/635,089, filed Jun. 27, 2017, 296 pages.
U.S. Appl. No. 15/209,486, filed Jul. 13, 2016, Eric Schulze.
U.S. Appl. No. 15/635,089, filed Jun. 27, 2017, Eric Schulze.
U.S. Appl. No. 16/392,331, filed Apr. 23, 2019, Eric Schulze.
U.S. Appl. No. 16/849,136, filed Apr. 15, 2020, Eric Schulze.
U.S. Appl. No. 15/804,131, filed Nov. 6, 2017, Eric Schulze.
U.S. Appl. No. 16/835,589, filed Mar. 31, 2020, Eric Schulze.

CONTROLLING PERMISSIONS FOR ACCESS TO USER INTERFACE FEATURES

This application is a continuation of U.S. patent application Ser. No. 16/835,589 filed on Mar. 31, 2020, which is a divisional of U.S. patent application Ser. No. 15/804,131 filed on Nov. 6, 2017 (U.S. Pat. No. 10,642,451, issued on May 5, 2020).

This description relates to the descriptions in the following United States patent application and patent, the entire contents of all of which are incorporated here by reference: U.S. Ser. No. 14/272,021, filed May 7, 2014; and U.S. Pat. No. 9,705,931, issued Jul. 11, 2017.

BACKGROUND

This description relates to computer control of access to fields and features of an application.

SUMMARY

In general, in an aspect, an electronic system includes a processor and machine-readable hardware storage storing instructions executable by the processor to perform operations including the following: Instances of at least one type of page of a user interface are presented to at least a first user and a second user. Each of the instances of the type of page includes a current scope of user interface elements. All of the instances of a given type of page have current scopes of user interface elements that are the same as or subsets of a prototype scope of user interface elements for that type of page. Information is persistently stored representing a permitted scope of user interface elements that are available to each corresponding user in the user interface. The permitted scope of the second user is the same as or a subset of the permitted scope of the first user. Selections of user interface elements to be included in an updated scope of user interface elements for a particular instance of the type of page are received from the first user. The selections include only user interface elements that belong to both the prototype scope for that type of page and the permitted scope of the first user. The updated scope is persistently stored.

Implementations may include one or combinations of two or more of the following features. The user interface elements include at least one field. The user interface elements include at least one control. The user interface elements expose corresponding facilities of an application. The at least one of the user interface elements includes a field and the corresponding facility of the application includes a field of data values. At least one of the user interface elements includes a control and the corresponding facility of the application includes a function of the application. A list of the user interface elements that belong to both the prototype scope for that type of page and the permitted scope of the first user is presented to the first user. Each of the user interface elements in the list is associated with a selection control to indicate whether the element is to be included in the updated scope. The selection control includes a check box. Each of the user interface elements in the list is associated with an indicator of whether the element is to be exposed in the user interface for the instance of the type of page. The instance of the type of page for which the selections are being made is presented to the first user to be viewable simultaneously with the list of the user interface elements. The presentation of the instance of the type of page for which the selections are being made is updated in real time according to the selections.

In general, in an aspect, instances of at least one type of page of a user interface are presented to two or more users. Each of the instances of the type of page includes a current scope of user interface elements. All of the instances of a given type of page have current scopes of user interface elements that are the same as or subsets of a prototype scope of user interface elements for that type of page. Information is persistently stored representing a permitted scope of user interface elements that are available to each corresponding user in the user interface. The permitted scope of a first user is the same as or a subset of the permitted scope of a second user, and receiving from the first user selections of user interface elements to be included in an updated scope of user interface elements for a particular instance of the type of page. The selections include only user interface elements that belong to both the prototype scope for that type of page and the permitted scope of the first user. The updated scope is stored persistently.

In general, in an aspect, an electronic system includes: a processor; and machine-readable hardware storage storing instructions executable by the processor to perform operations including the following. A page of a user interface is presented including a current scope of user interface elements suitable for a second user of the page, the page being presented to a first user. A list of user interface elements is presented to the first user that includes at least the user interface elements of the current scope. Selections are received from the first user of user interface elements of the list to be included in an updated scope of user interface elements for the page. The list of user interface elements is cropped to include in the updated scope only the ones selected by the first user to be included in the updated scope. The updated scope is stored persistently.

Implementations may include one or combinations of two or more of the following features. Before the cropping, the list includes user interface elements that belong to both a prototype scope of user interface elements for the page and an available scope of user interface elements for the first user. The cropping is in response to an action by the first user. The action by the first user includes exiting from the page. After the cropping, the page is presented to the second user including the updated scope. The updated scope includes part of an available scope of user interface elements for the first user.

In general, in an aspect, a page of a user interface includes a current scope of user interface elements suitable for a first user of the page. The page is presented to a first user. A list of user interface elements is presented to the first user that includes at least the user interface elements of the current scope. Selections are received from the first user of user interface elements of the list to be included in an updated scope of user interface elements for the page. The list of user interface elements is cropped to include in the updated scope only the ones selected by the first user to be included in the updated scope. The updated scope is stored persistently.

In general, in an aspect, an electronic system includes: a processor; and machine-readable hardware storage storing instructions executable by the processor to perform operations that include the following. A request is received by a first user to have access to a user interface of an application in a first mode. The user interface is associated with a second user. The first user is given access to the user interface in a second mode by logging into the application as the second user. The user interface in the first mode has a first scope of user interface elements that are available to the first user. The user interface in the second mode includes a second scope of user interface elements that are available to the second user.

The first scope is the same as or larger than the second scope, and in the first mode selections are received from the first user of user interface elements in the first scope to be included in an updated version of the second scope.

Implementations may include one or a combination of two or more of the following features. The receiving of the request of the first user to have access to the user interface includes receiving a login by the first user that is different from a login that the second user would use to access the user interface in the second mode. The login by the first user uses credentials of the second user. The login by the first user includes a login TO the account of the second user.

In general, in an aspect, a request is received of a first user to have access to a user interface of an application in a first mode. The user interface is associated with a second user. The second user is given access to the user interface in a second mode by logging into the application as the second user. The user interface in the first mode has a first scope of user interface elements that are available to the first user. The user interface in the second mode includes a second scope of user interface elements that are available to the second user. The first scope is the same as or larger than the second scope. In the first mode selections are received from the first user of user interface elements in the first scope to be included in an updated version of the second scope.

Other aspects, implementations, features, and advantages, and combinations of them, can be expressed as methods, apparatus, systems, components, means and steps for performing the function, program products, software, business methods, and in other ways.

Other aspects, features, implementations, and advantages will become apparent from the following description, and from the claims.

DESCRIPTION

Figure 2:
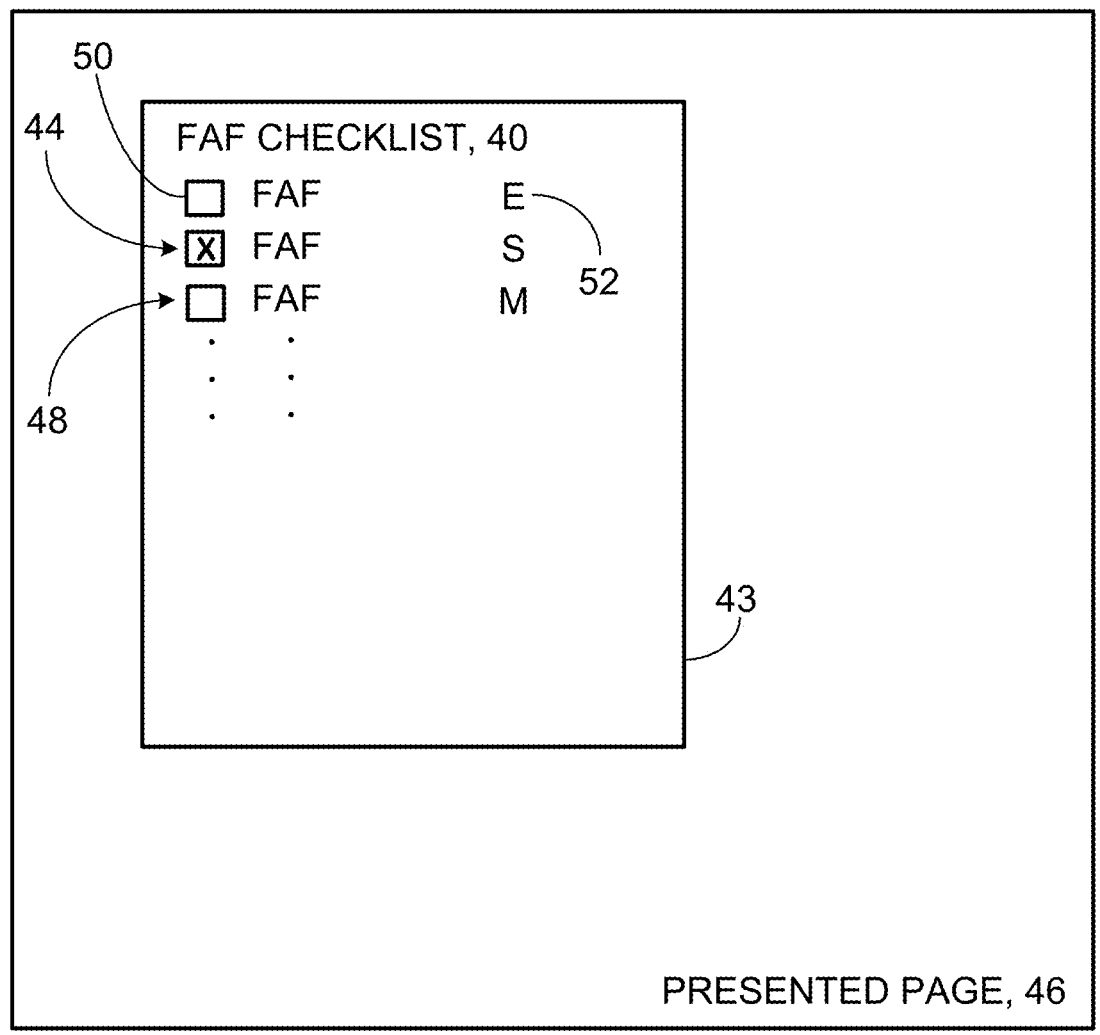
Figure 3:
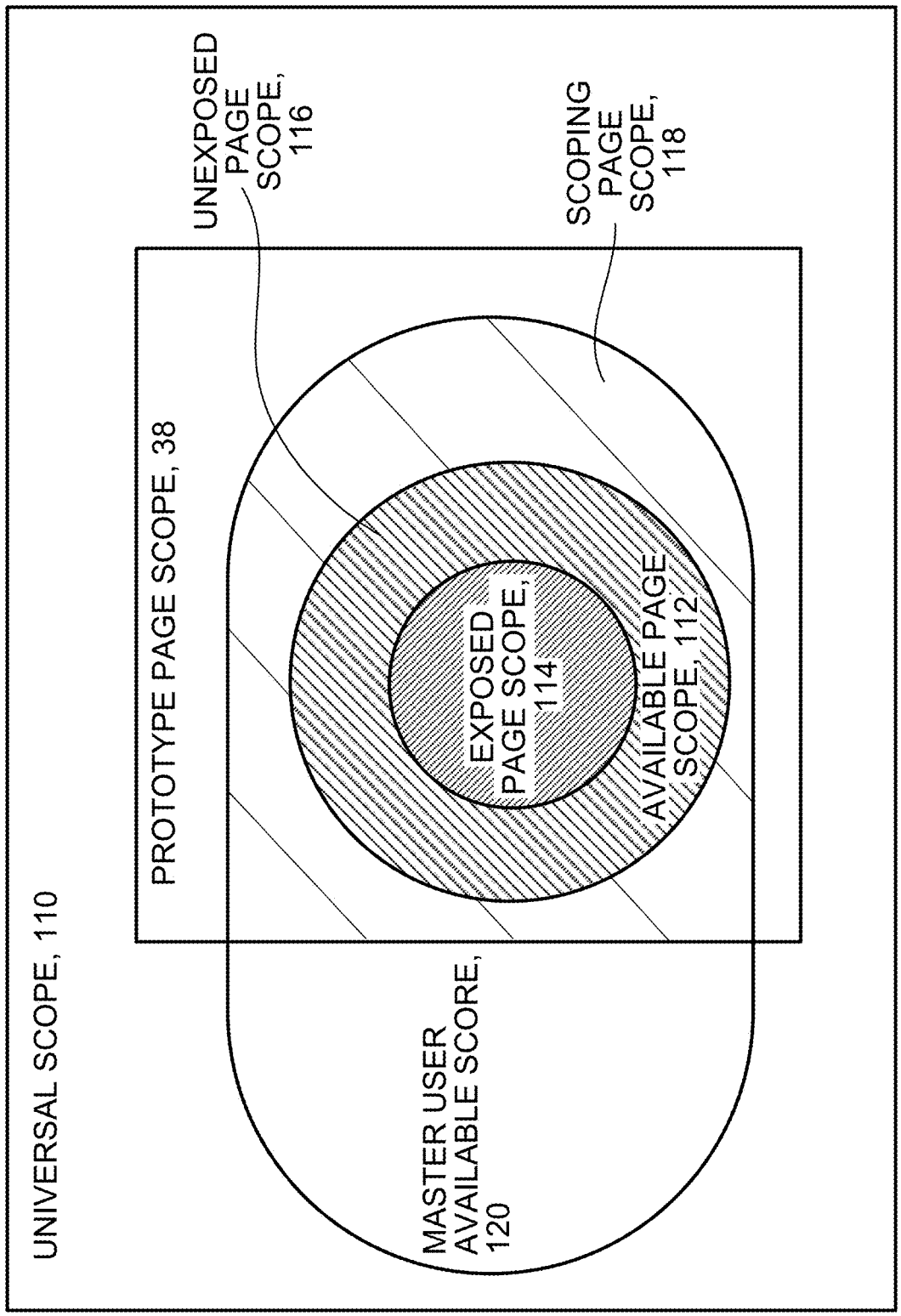
Figure 4:
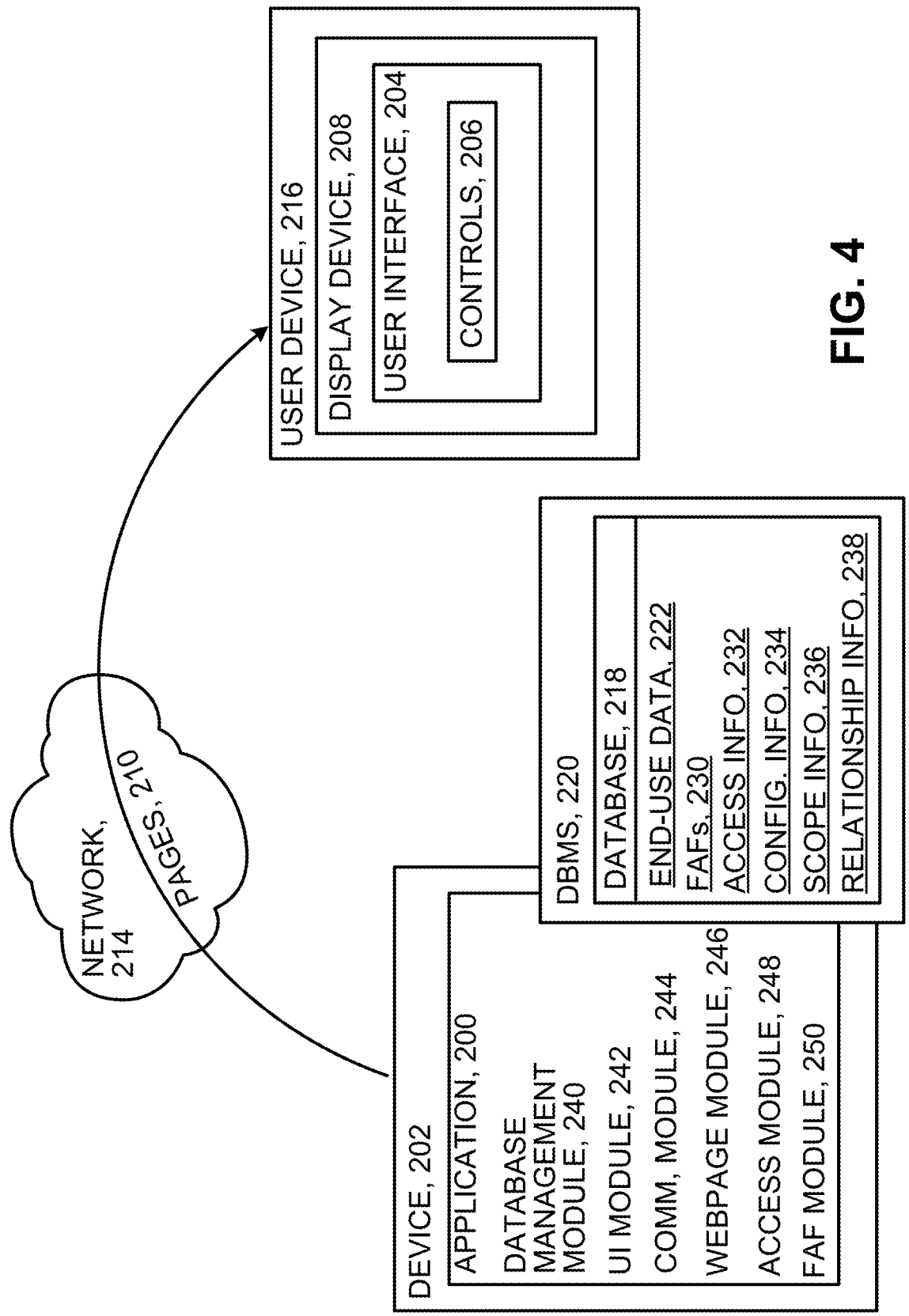

FIG. 1 is a block diagram
FIG. 2 is a Venn diagram.
FIG. 3 is a schematic diagram of a user interface.
FIG. 4 is a block diagram.

Health care providers, banks, retailers, and other enterprises often host applications used by their employees to do their jobs. A typical application can be presented to these users as pages, such as Web pages, through a Web browser or other user interface. The pages often present data and other information and also enable the user to update, add to, and change the information and to control the operation of various functions of the application using displayed buttons, menus, and other controls. The information presented to the users is frequently drawn from databases maintained by the enterprise and may be updated as a result of the users' work.

Different types of pages can be designed to enable the users to perform different tasks, for example, an order entry page, a patient status page, or a financial account configuration page. A given type of page also can be presented in various versions to different users to accommodate the different responsibilities, authorities, and work that they do. For this purpose the different types of pages and the different versions of a page can be configured to have somewhat different sets of controls and kinds of information that they present.

In some enterprises, employees have rigid or informal hierarchical relationships to one another that are reflected in the tasks that they do as they work in the different versions of a page. For example, a chief radiologist may have the authority to review and supplement a report written by a staff radiologist. The staff radiologist may use one version of a report writing page that includes a set of information and controls while the chief may use a richer version of that same report writing page that exposes more information and more controls to him.

Ideally the information and controls exposed to each user in his version of each page of the interface are chosen in a way to enable him to work efficiently and effectively. In addition, the information and controls for each version of each page must not include items that a given user should not have accessible. For example, a supervisor order taker for a retail enterprise may have the power to allow a discount to customers on an order entry page but a staff order taker may not be allowed to do so.

It would be useful to be able to configure each version of each page so that it included exactly the items that would be suitable for the job to be done by the user, no more and no fewer, and excluded items that, for security, quality control, or other reasons, should not be made available to the user.

In many applications, the authority to configure the versions of the pages is generally limited to the application developer or to a very small number of trusted administrative employees who are not actually doing the kinds of work done by the users for whom they are configuring the pages.

In a large enterprise, the array of functions and information that might be exposed to users of an application can be very large and complex.

As a result of these factors, a typical application only provides very limited mechanisms for changing the configurations of pages seen by users and users are typically grouped by title or responsibility in order to simplify the global task of configuring the pages.

U.S. Pat. No. 9,705,931 described elegant and powerful ways to enable any user of an application (not merely the developer) to configure pages for one or more other users and in doing so to treat every user differently from every other user and to determine whether each individual item of information and each possible function of the application should be made available to a user for a particular page. This system provides a unique and highly powerful way to configure the pages presented by an application, yet its capabilities are so flexible and fine grained that in some practical uses it can be daunting for a user to configure pages for other users.

Here we describe significant technological improvements to the techniques presented in the patent that make the process by which a user configures pages for other users not only elegant and powerful but also simple and intuitive. Although we sometimes describe these improvements as they would be applied to or used with the specific techniques recited in the patent, they also could be applied to and used with other systems in which users configure pages for other users.

As shown in FIG. 1, in implementations of the technology that we describe here, a software application 10 can expose fields 14 and features 16 to users 12 through user interface pages 13.

Each field can be, for example, a particular field 18 of a table 20 of a database 22 managed by the application. Such a field can be exposed to the user by presenting the field as a column 24 of a displayed table 26 and by presenting data values 28 in that field column for records 30.

Each feature of the application can be exposed to a user by presenting a corresponding user interface control 31 (such as a button, check box, or link) in the user interface.

We use the term "field" broadly to include, for example, any type or class or form of data or other information of any kind, whether or not contained in a database or expressed in database terms.

We use the term "feature" broadly to include, for example, any function, operation, capability, method, computation, analysis, presentation, or other process that can be implemented or provided by an application.

We use the term "user interface control" (or sometimes simply "control") broadly to include, for example, any button, menu, menu item, object, icon, link, context sensitive item, check box, radio button, drop down list, data entry field, or any other device through which a user can invoke, or control the operation of, a feature of an application.

We use the term "present" broadly to include, for example, to make a field or a feature apparent or perceptible to a user visibly or audibly.

We use the term "expose" broadly to include, for example, any method, mode, or manner of presenting a field or feature to a user. A field, for instance, can be exposed by presenting the field or a data value for the field, or an array, table, or spreadsheet including the field or data values or other information, among other ways. In some cases, exposing a field can include accepting an update, change, or new data value from a user through the user interface. A feature can be exposed by presenting a control for the feature.

We use the term "FAFs" broadly to include, for example, one or more fields and features.

We use the term "scope" broadly to include, for example, any range, spectrum, group, array, set, subset, or universe of FAFs that may be, for example, available to or exposed to users through user interfaces. A scope can be associated with a user or with a page of a user interface. FIG. 3 is a Venn diagram of certain relationships of example scopes.

We use the term "universal scope" 110 (FIG. 3) broadly to include, for example, all of the FAFs of a given application. The universal scope may be available and exposed only to universal users of which there would typically be only one or very few.

We use the term "available" broadly with respect to FAFs to include, for example, any FAF that is within the ability or authority of a user to take advantage of, make use of, or expose or remove from exposure on a user interface, among other things.

In some cases, FAFs are exposed to users in Web pages 32 through a Web browser 34. Different types of pages—for example, worklist, report, workflow, and viewer pages—can expose different scopes of FAFs to enable users to perform different tasks on the different pages. Furthermore, the FAFs exposed on pages of a given type can be different for different users, depending, for example, on their job titles or responsibilities.

We use the term "page" broadly to include, for example, any assembly of user interface elements that are presented together through a user interface, such as a Web page.

A particular type of page of the user interface can be represented by a "page prototype" 36 that has a "prototype page scope" 38. The actual pages presented to users in a user interface ("presented pages" 32) are instances of corresponding page prototypes. The prototype page scope for a given page prototype defines those FAFs (belonging to the universal scope) that are permitted to be available to one or more users of presented pages for that page prototype. Any FAF that is not part of the prototype page scope of the page prototype is not permitted to be available to any user of any corresponding presented page. The characteristics of each FAF are imparted to the FAF during the design of and as part of the application.

Each presented page for a given user has an "available page scope" 112 (FIG. 3). The available page scope of a presented page is all or a subset of the FAFs that are in the prototype page scope for that page. The available page scope of each presented page may also include an "exposed page scope" 114 that encompasses the FAFs that are exposed to the user at a given time on the presented page. The exposed page scope may include any FAF that is in the available page scope of that presented page, and may include no other FAF. In some implementations a user is able to select and deselect each of the FAFs of the available page scope for inclusion in the exposed page scope of his own pages and in that way to exercise some degree of control over which available FAFs are exposed on the presented page. Sometimes this capability is exposed to the user in a list of FAFs within a window, such as a FAF checklist described later.

Each user has an "available user scope". We use the term "available user scope" broadly to include, for example, all of the FAFs that are available to that user at a given time across all of the pages of the user interface.

In configuring the pages of a user interface of an application for effective use by various users of an enterprise, it is useful to be able to configure, for each presented page for each user, an available page scope and an exposed page scope that enable the user to perform a task on that page effectively, efficiently, and appropriately given his position and the task. (Among other goals, it may be useful to prevent certain users from using FAFs of a given prototype page that they don't need or could be risky for them to use.)

In some cases, a user ("master user") can engage in a "scoping process" to define, change, or update the available page scope of a presented page of another user ("subordinate user"). The master user can do so if (and typically only if) the available user scope of the master user includes all of the FAFs that belong to the available user scope of the subordinate user for that page.

We use the term "scoping process" broadly to include, for example, any activity in which one or more scopes is set, determined, defined, changed, or updated.

In some cases, the exposed page scope after the scoping process will be the same as the available page scope and include all of its FAFs, unless and until the subordinate user chooses to remove one or more of the FAFs of the available page scope from the exposed page scope. Typically the subordinate user, however, can never add FAFs to his own available page scopes.

In some examples, during the scoping process, the master user also can define the exposed page scope of a presented page by indicating which of the FAFs of the available page scope are to be in the exposed page scope, at least as of the time when the subordinate user next logs in to the application.

Any FAFs that are in the subordinate user's available page scope but not in his exposed page scope are not exposed to the user (the "unexposed page scope" 116). The exposed page scope and the unexposed page scope together make up the entire available page scope for a presented page.

Although a master user and a subordinate user can have any kind of relationship of their positions, titles, and authorities in an entity, in some cases, the master user is a supervisor of or otherwise at a higher level in an organizational hierarchy than the subordinate user. For example, the master user can be a chief radiologist and the subordinate user can be a staff radiologist.

During the scoping process the master user can choose which FAFs are to be included or excluded from the available page scope of the subordinate user by choosing those FAFs from a "scoping process scope" 118.

In some implementations, the scoping process scope (shown by cross hatching in FIG. 3) is the intersection of (that is, belongs to both) the prototype page scope for that page and the master user's available scope 120. Constraining the FAFs that can be chosen for the available page scope to this scoping process scope helps to assure the following:

1. The number of FAFs that the master user must consider in the scoping process for each page is as small as possible and therefore easier to work with, because, even if the master user's available scope is large, only the FAFs that are also in the prototype page scope are included in the scoping process scope.

2. The FAFs that can be included by the master user are only those that have been predetermined to be appropriate for the prototype page scope for that page.

3. The master user cannot include any FAFs that he does not himself have available and therefore cannot extend his authority beyond its intended range.

Some implementations provide a simple, easy-to-use mechanism to show the master user which FAFs are within the scoping process scope and enable the master user to select or unselect each of the FAFs for inclusion in the available page scope.

As shown in FIG. 2, in some cases this mechanism is a FAF page checklist 40 presented, for example, in a sub-window 42 that is visible at the same time that the corresponding presented page 46 is visible. All FAFs in the scoping process scope are shown continuously to the master user during the scoping process whether they have been selected for inclusion in the available page scope or deselected. A wide variety of other mechanisms could be used to enable the master user to work on the scoping process.

In some examples, the master user begins the scoping process by logging in TO the subordinate user's account by invoking a control on the master user's presented pages, for example, by clicking a button labeled "Log In To." Then the master user can select a subordinate user from a subordinate user list. The users on the subordinate user list are only those users for whom the available page scopes of all presented pages are the same as or subsets of the master user's available scope. In other words, the master user cannot log in TO a subordinate user who has more available FAFs on any presented page than would the master user by virtue of the master user's available scope. The universal user can log in TO any other user's account.

In some implementations, once the master user has selected a subordinate user, the system automatically logs in TO that subordinate user's account without requiring the master user to have knowledge of the login credentials of the subordinate user. Because the log in TO feature is itself a FAF, requirements for using the feature can be specified in the design of the FAF including restrictions that could require the master user to present the login credentials of the subordinate user's account. In some examples, the master user could login TO an "origin account" representing a group of users composed of the origin user and "clones" of the origin user. Requiring a master user to enter the login credentials of the origin account would enable an enterprise to use the login credentials to control the authorities of respective master users to manage the available page scopes only of groups for which they know the origin account login credentials. For example, a chief radiologist could be given the login credentials for all radiologists who are origin or clone users of groups that report directly or indirectly to him, while those same login credentials could be withheld from the chief surgical nurse.

While the master user is logged in TO the subordinate user's account, he can see (and interact with each of the FAFs on) each of the presented pages of the user interface of the subordinate user (and navigate among them) as if the master user were the subordinate user. When a given page is displayed, the master user also can simultaneously engage in the scoping process with respect to that page. To do this, when viewing a given page, the master user can invoke an appropriate control, for example, by clicking on a button titled "FAF checklist." In response, the FAF page checklist 40 is opened in a sub-window 43.

As shown in FIG. 2, the FAF page checklist includes a list 44 of all of the FAFs 48 in the scoping process scope (for that page). All FAFs in the scoping process scope are maintained on that list throughout the scoping process. Next to each of the FAFs is a checkbox 50 that can be checked and unchecked repeatedly during the scoping process to indicate that a FAF is to be included (when checked) or excluded (when unchecked) in the available page scope.

Checked FAFs (except those that have been toggled to be unexposed) are displayed on the presented page and viewed by the master user in real time and simultaneously with the FAF page checklist, so that the master user can see the impact of each of the changes to the FAF page checklist. In some cases, the master user can right click on a control of the presented page to cause the exposed feature to be hidden (unexposed). Once a control is hidden, it can be exposed again by checking the corresponding box in the FAF page checklist or (if the available box is already checked) by toggling the FAF to the exposed state.

The scoping process makes it easier for the master user to understand the FAFs that the subordinate user typically uses because when the master user logs in to the subordinate user's account and navigates to a page he sees the exposed page scope immediately and accurately in the user interface. And as he adds or removes FAFs to or from the exposed page scope, he immediately sees the revisions in the exposed user interface.

In some implementations, the FAF page checklist could present the FAFs in a richer way to visually indicate, for each FAF on the checklist, whether the FAF is part of the subordinate user's exposed page scope (by showing, say, an E, 52), the subordinate user's unexposed page scope (by, say, an S in the check box), or a master user's unexposed page scope (using, say, an M). For each FAF on the checklist, the master user then could cycle through its status (E, S, and M) in addition to checking or unchecking the box.

Logging in TO a subordinate user's account is different from the more conventional logging in AS the subordinate user. Logging in AS a subordinate user merely allows a master user to "stand in the shoes" of the subordinate user, to be exposed to FAFs exactly as the subordinate user would be exposed to them, and to add and remove from the exposed FAFs only FAFs that are within the available page scope for that subordinate user.

The scoping process is an improvement on some examples of how the techniques described in the cited patent are used to define scopes. In some implementations of those techniques, the master user would work from his own presented pages to invoke a checklist of all FAFs in his available page scope for a page. For some master users, this checklist could include far more FAFs than would be appropriate to select for the subordinate user and therefore was cumbersome to review. Each time the master user changed the list of available FAFs for the subordinate user, he could check the accuracy of the scoping work only by logging in AS the subordinate user and checking the relevant presented page. If any error was found, the master user would then have to log out of the subordinate user's account and log in again as the master user to make corrections. This process of bouncing back and forth between the master user account and the subordinate user account could be so time-consuming and cumbersome (especially when the number of FAFs available to the master user was large) that the master user could become frustrated and not take advantage of the full power of his ability to define the scopes for the subordinate user.

At any time during the scoping process, the checked states of the boxes and the states of the indicators 52 will represent a current proposed state of the available page scope and exposed page scope of the page. In some implementations, a cropping process can be invoked to convert the proposed state to the active state of the available page scope and the exposed page scope for all of the pages of the subordinate user's user interface, and the subordinate user's available scope. After the cropping process, the new active state will apply when the subordinate user is logged in to his own account.

The cropping process removes from the FAF page checklist (and accordingly from the available page scope) those FAFs that the master user has unchecked. In general, any user can access his own FAF page checklist at any time and use the FAF page checklist checkboxes and other features to control which FAFs are available to or exposed to the user at that time.

Typically, the master user can invoke the cropping process when he exits the subordinate user's account. In the course of exiting, however, the master user can indicate that the proposed state should be ignored, in which case the previous active state will remain unchanged. Or the master user can trigger the cropping process by, for example, invoking a "crop" button, or simply logging out. During the cropping process, the checked FAFs in the scoping process scope will remain in and become part of the active state of the available page scope. Unchecked FAFs will be removed (cropped) from the active state of the available page scope. The invoking of the crop button causes an adjustment of active state, regardless of whether the active state represents and addition of or removal of FAFs from the previous active state.

In implementations that use the indicators 52 (FIG. 2), the crop process could provide controls to enable the master user to "crop on E" to cause only FAFs in the exposed page scope to be kept in the subordinate user's available page scope or "crop on E and S" so that the subordinate user's revised available page scope includes both exposed page scope FAFs and unexposed page scope FAFs. In both crop on E and crop on E and S, FAFs identified as M are removed from the subordinate user's revised available page scope (in the new active state).

The techniques that we describe here make the scoping process by the master user elegant, powerful, simple, and intuitive. The master user can define the page scopes of a subordinate user (for example, a user whose available page scopes are no more extensive than the master user's available scope) by simply interacting with the user interface of the subordinate user.

As shown in FIG. 4, in implementations of the technology that we describe here, an application 200 can be executed on one or more workstations, mobile devices, or servers 202. The user interface 204 and its controls 206 can be presented on a wide variety of display devices 208. In some implementations, the user interface can be served as pages 210 from a server 202 through the Internet or other network 214 to user devices 216 including workstations and mobile devices. The database 218 can be stored locally at a workstation, mobile device, or server on which the application is running, or can be located remotely from a workstation, mobile device, or server on which the application is running. The database can be managed by any of a wide variety of database management systems 220 and could be a distributed database. In addition to storing end-use data 222 (such as patient images and profile information), the database can store the definitions of FAFs 230, user account and access control information including login credentials 232, user interface presentation and configuration information 234, a wide variety of scope information 236 including the kinds described earlier, and information 238 about the relationships of master users, subordinate users, universal users, origin users, clone users, among others.

The application can be organized in modules or components each of which is responsible for executing a particular set of features. The modules could include a database management module 240, a user interface presentation module 242, a communication module 244, a webpage service module 246, an access control module 248, and a FAF management module 250, among others.

Other implementations are also within the ambit of the following claims.

For example, although we have used examples related to medical care, the technology that we have described can be applied in a wide variety of other industries, fields, and contexts. The technology has particular applicability to enterprises that have large numbers of employees with groups of them having the same or similar job titles and responsibilities and with the groups organized hierarchically. The technology is useful when employees of such an entity need to use pages of a user interface of an enterprise application and with different categories of employees should have access only to different sets of fields and features on those pages.

What is claimed:

1. A computer-implemented method comprising:
receiving a request from a first user account to perform a scoping process for a second user account;
determining a first available plurality of interface elements for a page of an application, the first available plurality of interface elements being interface elements available to the first user account for inclusion in the page when the page is provided to the first user account for display;
determining a second available plurality of interface elements for the page of the application, the second available plurality of interface elements being interface elements available to the second user account for inclusion in the page when the page is provided to the second user account for display;
determining an exposed plurality of interface elements for the page of the application, the exposed plurality of interface elements being interface elements included in the page when the page is provided to the second user account for display, wherein the exposed plurality of interface elements is a subset of the second available plurality of interface elements;
in response to the request, providing for display, to the first user account, a first version of the page of the application, the first version of the page comprising the exposed plurality of interface elements;

while the first version of the page is displayed, receiving user input indicating that a first interface element, included in the first available plurality of interface elements and excluded from the second available plurality of interface elements, is to be included in the second available plurality of interface elements; and in response to the user input, adding the first interface element to the second available plurality of interface elements;

receiving a second user input indicating a crop selection, and in response to the second user input, removing one or more interface elements from the second available plurality of interface elements, to cause the second available plurality of interface elements to match the exposed plurality of interface elements.

2. The computer-implemented method of claim 1, wherein the user input indicates that the first interface element is to be included in the exposed plurality of interface elements, and wherein the method comprises:

updating, in real time as the user input is received, the display of the first version of the page, to display the first interface element.

3. The computer-implemented method of claim 1, comprising:

while the page is displayed, receiving a selection, on the first version of the page, of a second interface element that is included in the exposed plurality of interface elements, and in response to the selection, removing the second interface element from the exposed plurality of interface elements.

4. The computer-implemented method of claim 3, wherein removing the second interface element from the exposed plurality of interface elements comprises retaining the second interface element in the second available plurality of interface elements.

5. The computer-implemented method of claim 3, wherein the selection of the second interface element comprises a click on the second interface element.

6. The computer-implemented method of claim 1, wherein the second available plurality of interface elements is a subset of the first available plurality of interface elements, and wherein the first user account is permitted to provide the request to perform the scoping process based on the second available plurality of interface elements being the subset of the first available plurality of interface elements.

7. The computer-implemented method of claim 1, wherein the first interface element is configured to initiate the scoping process in response to selection of the first interface element.

8. The computer-implemented method of claim 1, wherein the addition of the first interface element to the second available plurality of interface elements in response to the user input maintains the first interface element excluded from the exposed plurality of interface elements.

9. The computer-implemented method of claim 1, wherein the user input comprises cycling between including the first interface element in the second available plurality of interface elements and excluding the first interface element from the second available plurality of interface elements.

10. The computer-implemented method of claim 9, wherein a current status of the first interface element with respect to the second available plurality of interface elements is indicated by a visual indicator that changes during the cycling.

11. An electronic system, comprising:

a processor; and machine-readable hardware storage storing instructions that, when executed by the processor, cause the processor to perform operations comprising:

receiving a request from a first user account to perform a scoping process for a second user account;

determining a first available plurality of interface elements for a page of an application, the first available plurality of interface elements being interface elements available to the first user account for inclusion in the page when the page is provided to the first user account for display;

determining a second available plurality of interface elements for the page of the application, the second available plurality of interface elements being interface elements available to the second user account for inclusion in the page when the page is provided to the second user account for display;

determining an exposed plurality of interface elements for the page of the application, the exposed plurality of interface elements being interface elements included in the page when the page is provided to the second user account for display, wherein the exposed plurality of interface elements is a subset of the second available plurality of interface elements;

in response to the request, providing for display, to the first user account, a first version of the page of the application, the first version of the page comprising the exposed plurality of interface elements;

while the first version of the page is displayed, receiving user input indicating that a first interface element, included in the first available plurality of interface elements and excluded from the second available plurality of interface elements, is to be included in the second available plurality of interface elements; and in response to the user input, adding the first interface element to the second available plurality of interface elements;

receiving a second user input indicating a crop selection, and in response to the second user input, removing one or more interface elements from the second available plurality of interface elements, to cause the second available plurality of interface elements to match the exposed plurality of interface elements.

12. The electronic system of claim 11, wherein the user input indicates that the first interface element is to be included in the exposed plurality of interface elements, and wherein the operations comprise:

updating, in real time as the user input is received, the display of the first version of the page, to display the first interface element.

13. The electronic system of claim 11, wherein the operations comprise:

while the page is displayed, receiving a selection, on the first version of the page, of a second interface element that is included in the exposed plurality of interface elements, and in response to the selection, removing the second interface element from the exposed plurality of interface elements.

14. The electronic system of claim 13, wherein removing the second interface element from the exposed plurality of interface elements comprises retaining the second interface element in the second available plurality of interface elements.

15. The electronic system of claim 13, wherein the selection of the second interface element comprises a click on the second interface element.

16. The electronic system of claim 11, wherein the addition of the first interface element to the second available plurality of interface elements in response to the user input maintains the first interface element excluded from the exposed plurality of interface elements.

17. The electronic system of claim 11, wherein the user input comprises cycling between including the first interface element in the second available plurality of interface elements and excluding the first interface element from the second available plurality of interface elements.

18. The electronic system of claim 17, wherein a current status of the first interface element with respect to the second available plurality of interface elements is indicated by a visual indicator that changes during the cycling.

\* \* \* \* \*